(12) United States Patent
Arndt et al.

(10) Patent No.: US 7,055,388 B2
(45) Date of Patent: Jun. 6, 2006

(54) ULTRASONIC SENSOR SYSTEM FOR HORIZONTALLY POLARIZED TRANSVERSAL WAVES

(75) Inventors: Volker Arndt, Erbach (DE); Michael Lach, Erkrath (DE); Michael Platte, Wuppertal (DE); Heinz-Ullrich Mueller, Michelstadt (DE)

(73) Assignees: Robert Bosch GmbH, Stuttgart (DE); Karl Deutsch Pruef-und Messgeraetebau GmbH & Co. KG, Wuppertal (DE)

( * ) Notice: Subject to any disclaimer, the term of this patent is extended or adjusted under 35 U.S.C. 154(b) by 73 days.

(21) Appl. No.: 10/470,979

(22) PCT Filed: Feb. 4, 2002

(86) PCT No.: PCT/DE02/00390

§ 371 (c)(1),
(2), (4) Date: Dec. 10, 2003

(87) PCT Pub. No.: WO02/061414

PCT Pub. Date: Aug. 8, 2002

(65) Prior Publication Data

US 2004/0083813 A1 May 6, 2004

(30) Foreign Application Priority Data

Feb. 2, 2001 (DE) ................ 101 04 610

(51) Int. Cl.
*G01N 29/04* (2006.01)
(52) U.S. Cl. .......................... 73/597; 73/602
(58) Field of Classification Search ................ 73/579, 73/597, 784, 594, 152.32, 599, 629, 632, 73/598, 602, 618, 627; 367/31, 30, 13; 219/109
See application file for complete search history.

(56) References Cited

U.S. PATENT DOCUMENTS

| | | | | |
|---|---|---|---|---|
| 3,101,608 A | * | 8/1963 | Benson et al. | 73/596 |
| 3,360,664 A | * | 12/1967 | Straube | 310/330 |
| 3,424,930 A | * | 1/1969 | Hans et al. | 310/338 |
| 4,245,172 A | | 1/1981 | Shirley | |
| 4,449,029 A | * | 5/1984 | Nied | 219/117.1 |
| 4,641,520 A | * | 2/1987 | Mao | 73/152.58 |
| 4,713,968 A | | 12/1987 | Yale | |
| 4,775,960 A | * | 10/1988 | Staron et al. | 367/31 |
| 5,303,588 A | | 4/1994 | Hamisch | |
| 5,383,365 A | * | 1/1995 | Buttram | 73/598 |
| 5,844,452 A | * | 12/1998 | Yamamoto et al. | 333/189 |
| 5,920,014 A | * | 7/1999 | Waschkies | 73/597 |
| 6,311,558 B1 | * | 11/2001 | Clark et al. | 73/643 |
| 6,351,991 B1 | * | 3/2002 | Sinha | 73/152.01 |

FOREIGN PATENT DOCUMENTS

| | | |
|---|---|---|
| DE | 198 15 041 C | 11/1999 |
| DE | 199 37 479 A | 3/2001 |
| EP | 0 653 061 B1 | 6/1998 |
| WO | 94 03799 A | 2/1994 |

* cited by examiner

*Primary Examiner*—Hezron Williams
*Assistant Examiner*—Jacques Saint Surin
(74) *Attorney, Agent, or Firm*—Michael J. Striker

(57) ABSTRACT

The invention relates to an ultrasonic sensor system, especially for controlling a resistance welding process. Said system comprises at least one receiver which is used to detect the ultrasonic signals from the area to be examined. At least two piezoelectric sensors (31, 32) are used as a receiver and are arranged in such a way that their polarization direction vectors indicate various directions, said vectors being projected in a plane perpendicular in relation to the propagation direction of an ultrasonic wave to be detected.

9 Claims, 5 Drawing Sheets

ULTRASONIC SENSOR SYSTEM FOR HORIZONTALLY POLARIZED TRANSVERSAL WAVES

BACKGROUND OF THE INVENTION

The present invention relates to an ultrasonic sensor system for controlling a resistance spot welding process according to the general class of the independent claim.

The essence of the method described in European Patent Application EP-A-653 061 is to investigate the intended weld region by ultrasonic transmission during the welding operation using shear and transversal waves by situating an ultrasonic transmitter and an ultrasonic receiver for shear waves on each of the external electrode adapters of the two diametrically opposed welding electrodes. Starting at the ultrasonic transmitter on one welding electrode, the ultrasonic signal passes through the weld material—two or more sheets to be welded—and the other welding electrode until it reaches the ultrasonic receiver. Said ultrasonic receiver converts said ultrasonic signal to a measurable electrical signal U, the temporal course of which can be depicted using the equation $U=U_O \cdot \sin \omega t$. In this equation, $\omega$ is the angular frequency of the ultrasonic wave, and t is the time. The through-transmission signal is detected online, and its amplitude $U_O$ is used as the control variable for amplitude and the shape of the welding current curve over time. The transversal wave is selected because the influence of fluid formation in the weld nugget on the dampening of a through-transmitted wave is very strong with this type of wave. The amplitude $U_O$ of the transversal wave—which changes markedly and in characteristic fashion over the course of the welding process—permits a reliable determination of the formation and size of the weld nugget and can therefore be used as a manipulated variable for a control process.

The basic feasibility of the method and the reliability of the examination findings are crucially dependent on the ultrasonic sensors used, their location relative to the welding electrodes, and the sound propagation inside the welding electrodes. In the realization according to EP-A-653 061, an arrangement of ultrasonic sensors is selected in which the ultrasonic transmitter and ultrasonic receiver are mounted on the external electrode adapters or on the electrode holders, which are not shown in the drawing. Shear waves, transversal waves, or torsional waves having a frequency of less than 1 MHz are generated. It is stated that it is particularly advantageous to generate horizontally polarized transversal waves, since they have a low tendency to undergo undesired mode changes when reflections occur inside the sound-directing electroder holder.

Transversal or shear waves propagate only in solid bodies, and not in fluids. In these types of waves, the particles or atoms oscillate perpendicular to the propagation direction of the wave. The direction of oscillation of the particles or atoms is also referred to as the polarization direction or, within an imagined coordinate system, as the polarization vector.

Transversal waves that propagate in the longitudinal direction inside a longitudinally-extending, laterally-limited solid body, e.g., a plate or a hollow cylinder, are said to be "horizontally polarized" when the polarization vector of the sound wave, i.e., the direction of oscillation of the particles or atoms, is parallel to one of the lateral limiting surfaces. If, for example, a transversal wave is coupled into part of the end surface of a hollow cylinder, which said transversal wave propagates in the axial direction of the cylinder, it is horizontally polarized if its polarization vector points in a tangential direction of the cylinder.

The ultrasonic transmitters and receivers are "shear wave test heads". They contain flat and, usually, round piezoelectric plates having a diameter ranging from a few mm to a few cm, and that execute a shearing motion when excited with electric voltage or, conversely, when they receive, they react to a received shear wave with a reception voltage. Since, when a shear wave test head of this type is mounted directly on the external electrode adapter, the main emission direction of the sound would not be directed in the direction of the weld material, but rather at the center of the electrode, wedge-shaped attachments are preferably used, that are installed between the test heads and the welding electrodes and permit the main emission direction of the test head to be oriented toward the weld material at an angle that is markedly less than 90°, e.g., approximately 45°. This is the only way to bundle an adequate portion of the sound energy toward the welding spot with this sensor arrangement.

German Patent Application DE-A-199 37 479, which was published at a later date, describes an ultrasonic sensor system that is improved in this regard. With said ultrasonic sensor system, the piezoelectric shear wave plate or the complete shear wave test head is installed in a recess inside the electrode adapter for transmitting and/or receiving. In fact, said piezoelectric shear wave plate or the complete shear wave test head is installed in such a manner that the piezoelectric plate is oriented nearly perpendicular to the electrode adapter, and the main emission direction of the transmitter and the main reception direction of the receiver are therefore parallel to the electrode adapter and are directed exactly at each other. This allows such a level of ultrasonic intensity to be produced in the welding spot and, during reception, it allows a received signal to be generated that is so great that an adequate wanted-to-unwanted signal ratio exists with regard for the further evaluation for controlling the welding process. Rectangular piezoelectric shear wave plates are used in this case. Basically speaking, however, they can have another geometric form (e.g., round, semicircular, or rhombic) as well.

Very generally speaking, if material areas to be examined are investigated by ultrasonic transmission using a separate ultrasonic shear wave transmitter and a separate ultrasonic shear wave receiver, there is always the difficulty that the transmitter and receiver must be directed at each other exactly with regard for the polarization direction of the shear wave produced. To provide the user with a rough orientation, the particular polarization directions are therefore always marked on the housing when shear wave test heads are used. In a transmitter-receiver arrangement, the polarization directions of the transmitter and receiver must match, because the two ultrasonic shear wave test heads behave, in terms of the amplitude of the electrical received signal, like two optical polarization filters in terms of the passage of light: if the two shear wave test heads are in exact parallel alignment and the maximum reception voltage is $U_O$, the reception voltage is $U(\alpha)$, depending on the angle $\alpha$ at which the two polarization directions are rotated relative to each other:

$$U(\alpha) = U_O \cdot \cos(\alpha) \cdot \sin(\omega t)$$

($\omega$=angular frequency, t=time)

When $\alpha=90°$, the amplitude $U_O \cdot \cos(\alpha)$ of the reception voltage $U(\alpha)$ is theoretically zero. Due to diffraction and refraction phenomena, and the natural sound field characteristics of a piezoelectric disk, however, a finite value is still usually measured for $U(\alpha)$ when $\alpha=90°$. Said value is so small, however, (1 to 10% of $U_O$), that the received signal can no longer be reliably evaluated.

These facts also affect the sensor systems described hereinabove for monitoring a resistance spot welding process, in particular: the polarization directions of the ultrasonic shear wave transmitter and receiver installed on the electrode adapters or integrated in the electrode adapters must be directed toward each other and mounted in such a manner that their polarization directions are parallel to each other. If not, the through-transmission amplitude is too low. When the shear wave sensors are mounted on the electrode adapters, or the electrode adapters are installed in the electrode holders when the sensors are integrated in the adapters, an adjustment step must be carried out. To do this, the sensors and/or the electrode adapters with the preinstalled sensors are turned, in a first rough step, until one can see that the markings of the polarization directions of the transmitter and receiver are parallel with each other. A fine adjustment is then carried out, again by turning the sensors or the electrode adapters. To do this, the reception voltage is observed and brought to a maximum value. This procedure is complicated, time-intensive, and fraught with error if it is not carried out with the proper level of care. It must be carried out by trained technicians, because the ultrasonic signal must be observed and interpreted as well, for control purposes. If the sensors or electrode adapters are worn, they cannot be simply replaced by untrained personnel. When the sensors are replaced, one must also put up with an undesirably long period of downtime of the welding machine because of the adjustment that must be carried out.

The object of the present invention is to provide a sensor system for shear waves that functions without having to set up the transmitter and receiver as described hereinabove, enabling the sensors to be replaced easily during initial installation or when they are worn, when they are used for controlling a resistance spot welding process.

The ultrasonic sensor system, in particular for controlling a resistance spot welding process, has at least one receiver that detects the ultrasonic signals from the area to be examined, whereby at least two piezoelectric sensors are used as a receiver that are arranged in such a way that their polarization direction vectors indicate various directions, said vectors being projected in a plane perpendicular to the propagation direction of an ultrasonic wave to be detected. This insures that at least one of the piezoelectric sensors detects a signal—that is different from zero—independently of the polarization direction of the wave to be detected. In particular, it is independent of how the receiver is positioned relative to the transmitter. As a result, complex adjustment procedures can be eliminated. The downtimes of resistance spot welding systems can therefore be greatly reduced.

In an advantageous further development, it is provided that the output variables of the at least two sensors be coupled in a signal processing unit accordingly in order to detect a measure of the amplitude of the ultrasonic wave. This coupling increases the sensitivity of the system. Using the types of coupling named in the further dependent claims, it can be insured that the output signal does not fall below a certain minimum level. This increases the reliability of the evaluation and, therefore, the quality of the controlling of the resistance spot welding process.

In an advantageous further development it is provided that the piezoelectric plates have a stacked configuration. This results in the absence of lateral misalignment, in particular, so that the sound field is absorbed by both piezoelectric plates at the same point. This makes the arrangement particularly suited for use with any spacially inhomogeneous ultrasonic wave field. The signal processing unit can make appropriate corrections to easily compensate for the phase displacement that occurs in terms of the sound propagation time.

The present invention provides that, rather than using a single piezoelectric shear wave receiver, a plurality of identical shear wave receivers are used, the polarization directions of which are located in a common plane, but that have various directions within the plane, so that a shear wave that is propagating at a right angle to this plane always delivers a received signal that is different from zero to at least one of the receivers, independently of its polarization direction in this plane, and that the reception voltages of the individual shear wave receivers are transmitted to an electronic circuit device that generates an output signal by suitably coupling the individual reception voltages, which said output signal is different from zero and is proportional to the amplitude of the shear wave to be received given any position of the polarization direction.

In terms the application for controlling a resistance spot welding process, the present invention is based, in particular, on the knowledge that a low-frequency (<1 MHz) shear wave that is introduced into the welding electrode—which is cylindrical and hollow inside in order to accommodate the cooling water—propagates more or less homogeneously through the entire cross section of the welding electrode on its way to the receiver on the other welding electrode. This is due to the fact that, with typical propagation speeds of 3000 m/s, the wavelength of the shear wave in the cylindrical shaft of the welding electrode ranges from a few millimeters to a few centimeters. Welding electrodes typically have an outer diameter of 15–30 mm, and their walls are typically 4–8 mm thick. The magnitude of the cross section of the electrode adapter is therefore equal to or smaller than that of the wavelength. The cross section of the welding electrode itself is already such a small aperture opening for the propagating ultrasonic wave that a nearly undirectional propagation of sound takes place, and the sound wave fills the entire cross section of the electrode adapter after just a short path of travel.

DESCRIPTION OF THE PREFERRED EMBODIMENTS

Figure 1:
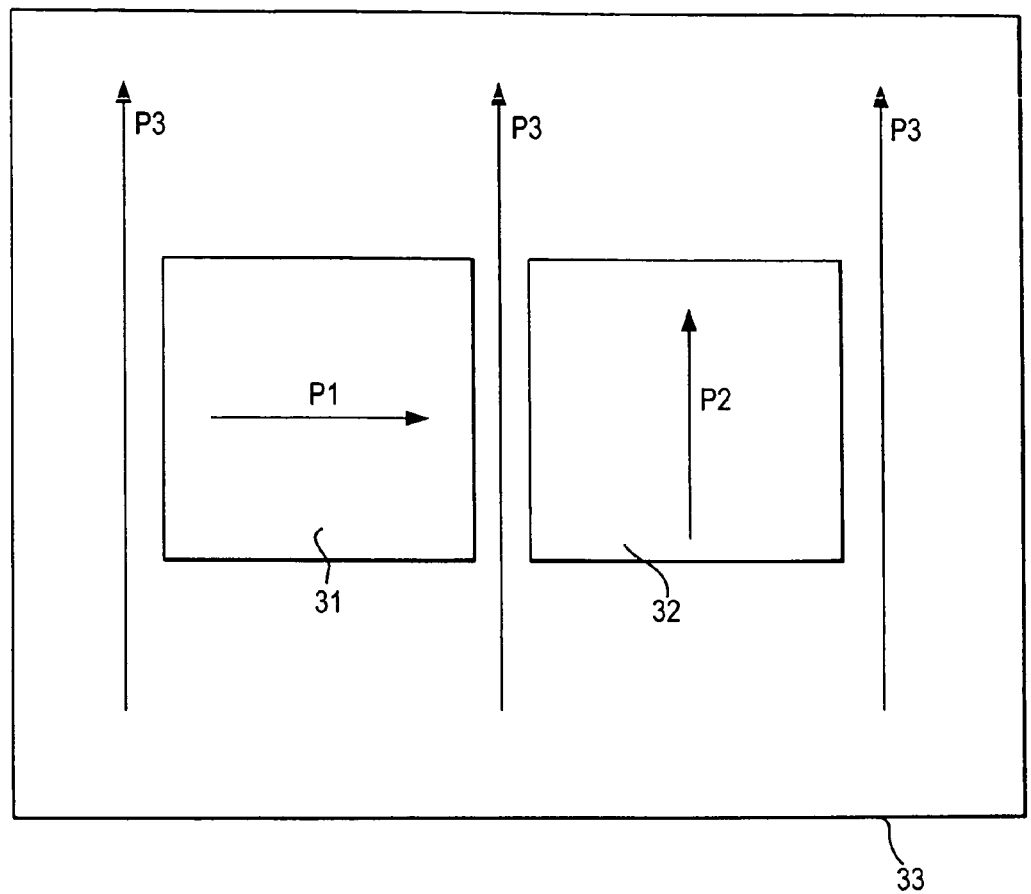
FIG. 1 shows the fundamental mode of operation of the sensor system using, as an example, two piezoelectric disks that are positioned at a 90-degree angle relative to each other.
Figure 1:
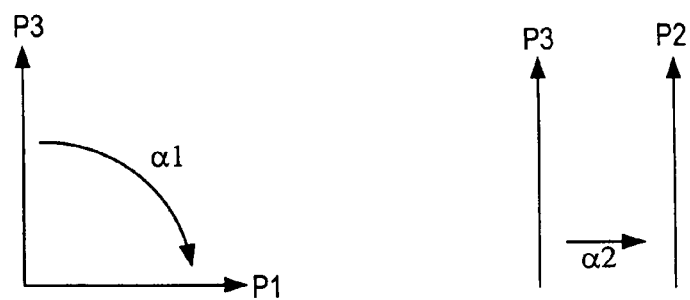

FIG. 1 shows the fundamental mode of operation of the sensor system, according to the example, using the simplest example of two piezoelectric disks, 31 and 32, that are positioned at a 90-degree angle ($\alpha1-\alpha2$) relative to each other. The two piezoelectric disks 31 and 32, that are designed as shear wave oscillators, are positioned, as receivers, in a shear wave field that may be homogeneous within the area enclosed by line 33. The propagation direction of the shear wave extends perpendicular to the plane of the paper. P1 and P2 are the polarization vectors (and polarization directions) of the two piezoelectric disks 31 and 32. P3 is the polarization vector of the shear wave that is passing through the plane of the paper. $\alpha 1$ is the angle that exists between the polarization vector P3 of the shear wave and the polarization vector P1 of the first piezoelectric disk 31. $\alpha 2$ is the angle that exists between the polarization direction P3 of the shear wave and the polarization vector of the second piezoelectric disk 32. This means that the reception voltages U1 and U2 of the shear wave sensors 31 and 32 are:

$$U1 = U_O \cdot \cos(\alpha 1) \cdot \sin(\omega t) = A1 \cdot \sin(\omega t)$$

$$U2 = U_O \cdot \cos(\alpha 2) \cdot \sin(\omega t) = U_O \cdot \cos(\alpha 1 - 90°) \cdot \sin(\omega t)$$
$$= U_O \cdot \sin(\alpha 1) \cdot \sin(\omega t) = A2 \cdot \sin(\omega t)$$

($\omega$=angular frequency of the ultrasonic wave, t=time)

Figure 2:
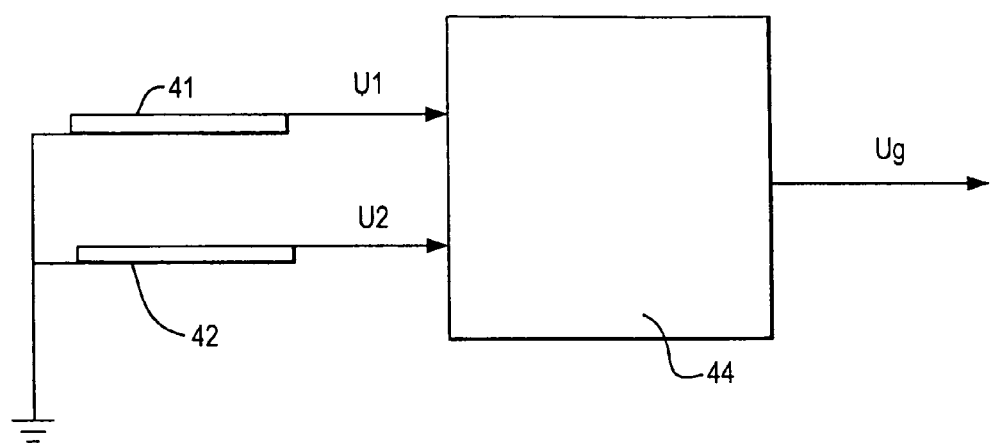
FIG. 2 shows the sensor system in combination with a circuit device.

Accordingly, of the amplitudes $A1 = U_O \cdot \cos(\alpha 1)$ and $A2 = U_O \cdot \sin(\alpha 1)$ of the received signals U1 and U2 of the two shear wave sensors or piezoelectric disks (31, 32), at least one of them is always different from zero. According to FIG. 2, the received signals U1 and U2 of the two shear wave sensors or piezoelectric disks 41, 42 are now forwarded to a circuit device 44 that can couple the individual received voltages in diverse fashions in such a manner that a single output signal Ug (e.g., Ug=Ag·sin($\omega$t)) results, the amplitude Ag of which is more or less independent of the polarization direction of the shear wave to be detected.

The same observations also apply, in a similar sense, when the piezoelectric shear wave plates used for reception in FIG. 1 are positioned so that they are tilted relative to the plane of the paper and form an angle $\gamma$ with the impinging wave front, which said angle $\gamma$ is different from zero. In this case, the same observations apply for the vectors of the polarization directions of the shear wave test heads or the shear wave piezoelectric plates, which said vectors are projected into the plane that is perpendicular to the propagation direction of the shear wave to be detected.

The following examples of coupling the received signals in the sense of the present invention are easy to carry out in terms of circuitry using analog, integrated circuits (IC's), or by digitizing the ultrasonic signals, followed by arithmetic operations:

a) First of all, signals U1 and U2 of the shear wave sensors or piezoelectric plates are squared and then added.

$$Ug = U1^2 + U2^2 = Uo^2 \cdot \cos^2(\alpha 1) \cdot \sin^2(\omega t) + Uo^2 \cdot \sin^2(\alpha 1)$$
$$\cdot \sin^2(\omega t) = Uo^2 \cdot \sin^2(\omega t)$$

Since $\cos^2(\alpha 1) + \sin^2(\alpha 1)$ is always equal to 1, the resultant amplitude of the received signal is always $Uo^2$, completely independent of angle $\alpha 1$, the squared reception voltage amplitude of an individual shear wave receiver with its polarization direction oriented parallel to the polarization direction of the shear wave to be detected.

b) Based on Case a), the result is extracted further:

$$Ug = \sqrt{(U1^2 + U2^2)} = Uo \cdot$$
$$\sqrt{\cos^2(\alpha 1) \cdot \sin^2(\omega t) + \sin^2(\alpha 1) \cdot \sin^2(\omega t)} = Uo \cdot |\sin(\omega t)|$$

In this case, the received signal Ug—independent of angle $\alpha 1$—always corresponds exactly to the received signal of an individual shear wave receiver with its polarization direction oriented in parallel with the polarization direction of the shear wave to be detected.

c) The absolute values (amounts) of the two reception voltages are determined and added:

$$Ug = |U1| + |U2| = Uo \cdot |\sin(\omega t)| \cdot (|\cos(\alpha 1)| + |\sin(\alpha 1)|)$$

This result is already fully sufficient as well when the polarization directions of the transmit and receive sensors are aligned with each other in fixed fashion, as is the case when they are used in resistance spot welding systems after the sensors are installed in the welding tongs: In this case, the amplitude of Ug would be $Uo \cdot (|\cos(\alpha 1)| + |\sin(\alpha 1)|)$, and, depending on the installation of the sensors and the angle ($\alpha 1$), it would always be between 1 and $\sqrt{2}$, but never 0. Independent of angle $\alpha 1$, an adequate reception voltage would therefore always be available without the polarization directions from the transmitter and receiver having to be directed toward each other.

d) The absolute values (amounts) of U1 and U2 can also be determined, first of all, then both amounts can be compared, and the greater of the two can then be used as the output signal Ug. In this case, the amplitude of Ug would always be between 1 and $(\sqrt{2})/2$:

$$Ug = \text{Max}(|U1|, |U2|) = Uo \cdot \sin(\omega t) \cdot \text{Max}(|\cos(\alpha 1)|, |\sin(\alpha 1)|)$$

Figure 3A:
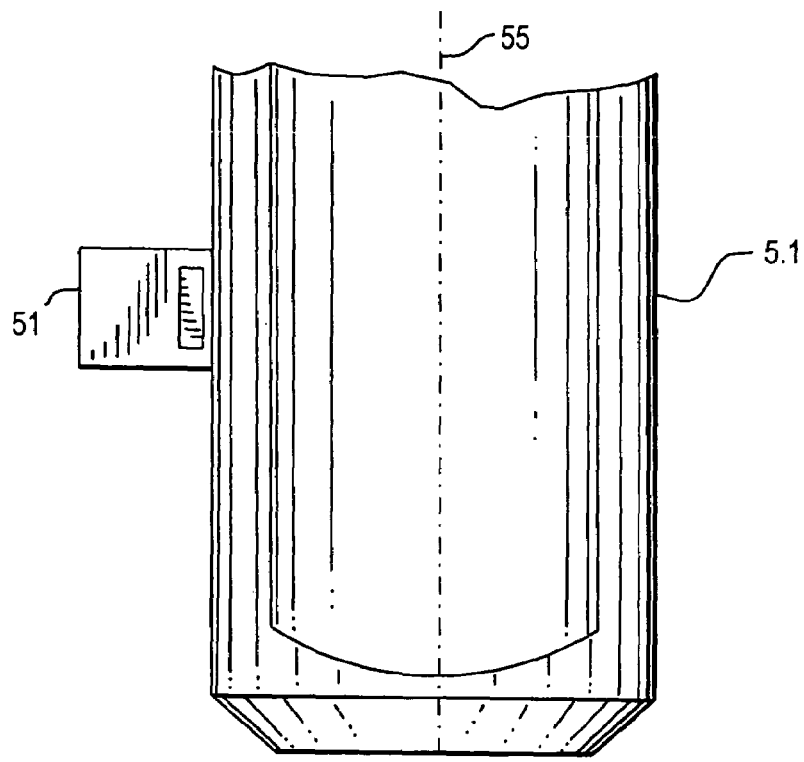
FIG. 3 shows a further sensor system outside of the welding electrode.
Figure 3B:
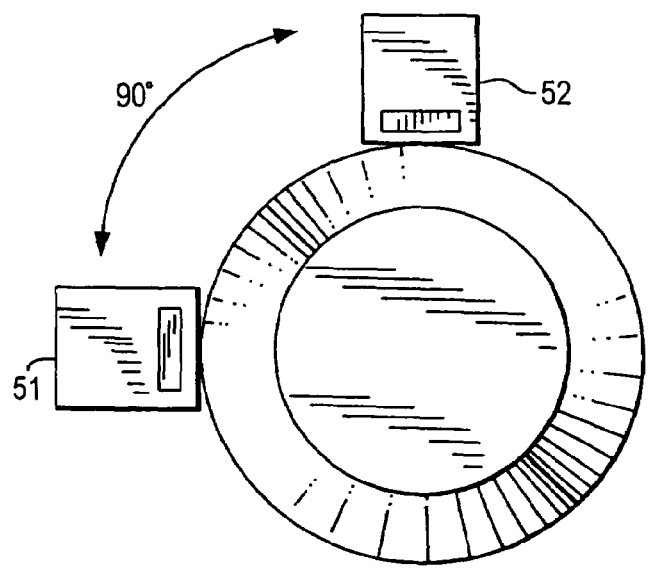

The arrangement of two or more receiving sensors, the reception voltages of which are processed further in appropriate fashion according to this invention, as described hereinabove, for example, can be realized in the most diverse fashion. If a sensor system according to EP-A-653 061 having shear wave test heads mounted on the lateral electrode adapter for controlling a resistance spot welding process is selected, then a second, identical shear wave test head 52 can be mounted on the electrode adapter 5.1 on the receiver side next to the first shear wave test head 51, as shown in FIG. 3. The installation site is so selected that the position is identical with regard for longitudinal axis 55 of the electrode adapter, and an angular displacement of only 90° (FIG. 3), for instance, exists in the plane perpendicular to longitudinal axis 55 of the welding electrodes.

Figure 4A:
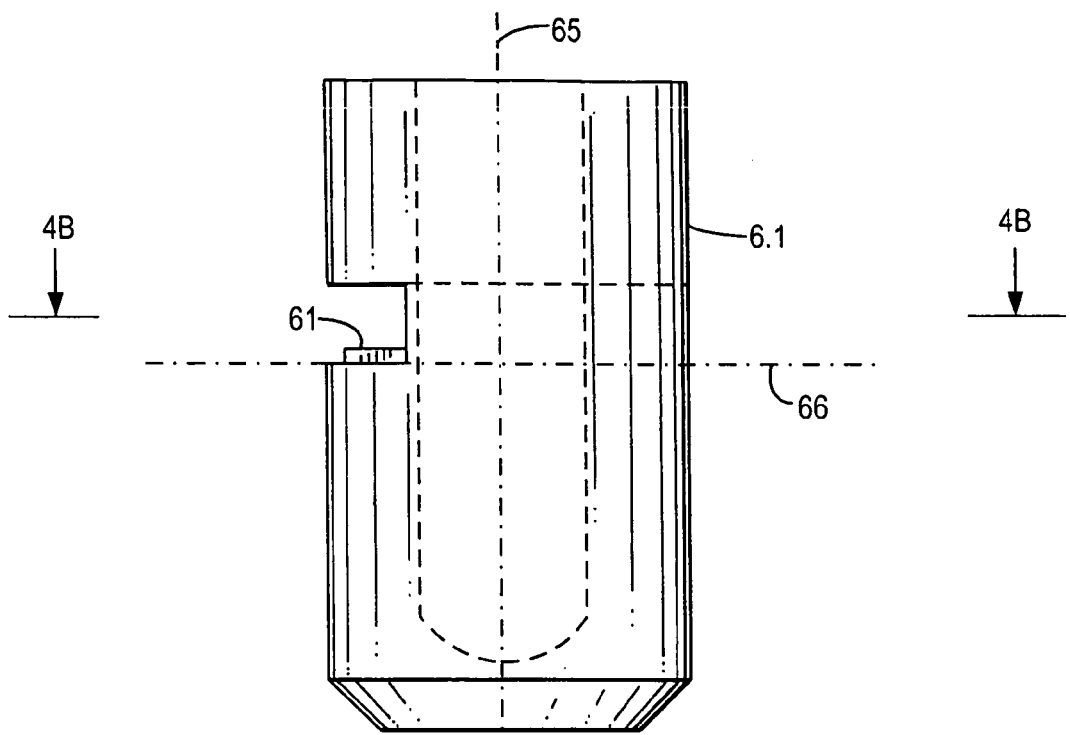
FIG. 4 shows a sensor system integrated in the welding electrode.
Figure 4B:
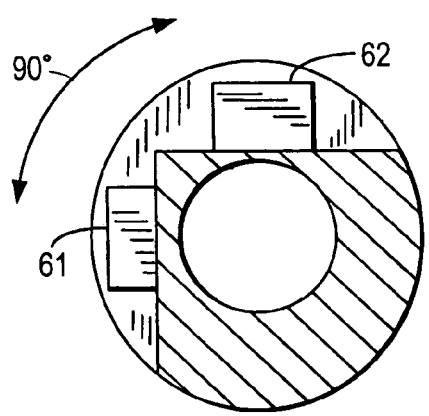

With a sensor system according to DE-A-1 99 37 479 having sensors integrated in the electrode adapters, two shear wave sensors having a polarization direction offset by 90° can be installed on the receiving side within a cross section 66 of electrode adapter 6.1 that lies in a plane 66 perpendicular to central axis 65 of the electrode adapter, e.g., by positioning two otherwise identical piezoelectric shear wave plates 61 and 62 offset by exactly 90° (FIG. 4).

Figure 5:
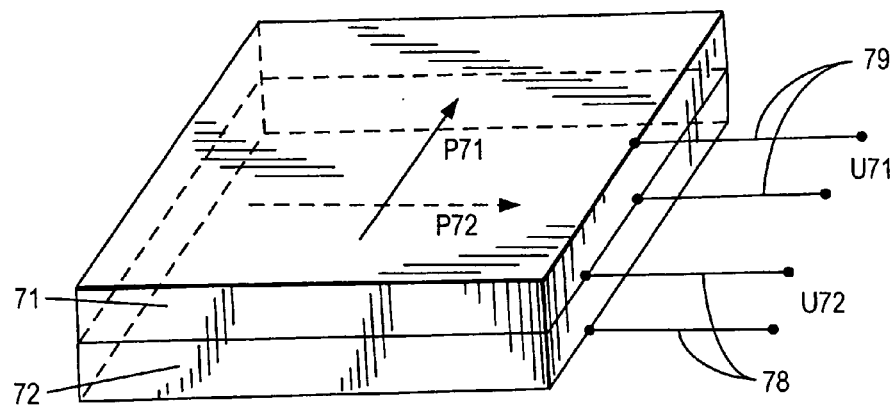
FIG. 5 shows a further sensor system having a stacked configuration.

Instead of positioning two or more shear wave receiving sensors side-by-side in the ultrasonic shear wave field, it is also fundamentally possible to position shear wave sensors in the same place in the sound field, which said shear wave sensors have polarization directions that are offset according to the invention. FIG. 5 shows this using a simple example, in which only two receiving sensors are used that have a polarization direction offset by 90°: In this case, the fact that piezoelectric transducers can also be configured and produced having a stacked design is utilized. Accordingly, in FIG. 5, two identical shear wave piezoelectric plates 71, 72 having polarization directions P71, P72 offset by 90° are stacked one on top of the other, in alignment with each other. The two shear wave piezoelectric plates 71, 72 are joined with each other in acoustically conductive fashion, e.g., by surface bonding or soldering. Electrical leads 78, 79 are so installed on the surfaces of the piezoelectric disks that the reception voltages U71, U72 of the two piezoelectric plates 71, 72 can be picked off separately at said electrical leads. Further details of the transducer construction, such as protective layers or dampening bodies, are designed in accordance with the related art. They are left out of FIG. 5, because they are not a subject of the invention, and they are not required any further to explain the mode of operation of the present invention.

It is true that ultrasonic test heads having a stacked configuration in accordance with FIG. 5 are basically more complex to manufacture in practice than conventional test heads having just one ply of piezoelectric elements. The present case has the advantage, however, that no lateral displacement whatsoever exists between the individual piezoelectric plates or sensors. Instead, the shear wave sound field is absorbed by both of the piezoelectric plates at the same point, except for a displacement in the sound propagation direction. This embodiment of the invention can therefore be used with every spacially inhomogeneous shear wave field as well. With reception voltages U71 and U72, the displacement in the sound propagation direction is realized only as a slight phase displacement in terms of sound propagation time, which said phase displacement can be compensated for or neglected electronically or arithmetically in the further processing of reception voltages, according to the invention, in a signal processing unit.

The invention is not limited to the use of a horizontally polarized transversal wave that is always bound to a lateral transfer medium (rod, plate, electrode adapter). The invention functions with any transversal wave, independently of whether it propagates in a limited or unlimited medium.

What is claimed is:

1. An ultrasonic sensor device of a spot welding system for controlling or monitoring a resistance welding process, the device comprising at least one receiver which detects ultrasonic signals from an area to be examined, said receiver being formed by at least two piezoelectric sensors that are arranged in such a way that their polarization direction vectors indicate various directions, said vectors being projected in a plane perpendicular to a propagation direction of an ultrasonic wave to be detected.

2. An ultrasonic sensor as defined in claim 1, wherein said sensors are arranged so that the polarization direction vectors are offset by 90°.

3. An ultrasonic sensor as defined in claim 1; and further comprising a signal processing unit to which output variables from said at least two sensors are transmitted and which delivers an output signal depending on the output variables of said sensors, which said output signal is a measure of an amplitude of the ultrasonic wave to be detected.

4. An ultrasonic sensor as defined in claim 1, wherein said sensors are located side-by-side in a plane.

5. An ultrasonic sensor as defined in claim 1, wherein said sensors are composed of piezoelectric plates that are stacked one on top of the other, in alignment with each other.

6. An ultrasonic sensor as defined in claim 1, wherein said sensors are integrated in a shaft of an electrode for resistance welding.

7. An ultrasonic sensor as defined in claim 1, wherein output variables from said sensors are coupled by adding amounts of individual signals.

8. An ultrasonic sensor device of a spot welding system for controlling or monitoring a resistance welding process, the device comprising at least one receiver which detects ultrasonic signals from an area to be examined, said receiver being formed by at least two piezoelectric sensors that are arranged in such a way that their polarization direction vectors indicate various directions, said vectors being projected in a plane perpendicular to a propagation direction of an ultrasonic wave to be detected, wherein output variables from said sensors are coupled by adding squared individual signals and/or determining a root of an addend.

9. An ultrasonic sensor device of a spot welding system for controlling or monitoring a resistance welding process, the device comprising at least one receiver which detects ultrasonic signals from an area to be examined, said receiver being formed by at least two piezoelectric sensors that are arranged in such a way that their polarization direction vectors indicate various directions, said vectors being projected in a plane perpendicular to a propagation direction of an ultrasonic wave to be detected, wherein output variables from said sensors are coupled by forwarding only a greater of individual signals for further processing.

* * * * *